(12) United States Patent
Hejazi et al.

(10) Patent No.: US 11,517,688 B2
(45) Date of Patent: Dec. 6, 2022

(54) FLAVOR ARTICLE FOR AN AEROSOL DELIVERY DEVICE

(71) Applicant: RAI Strategic Holdings, Inc., Winston-Salem, NC (US)

(72) Inventors: Vahid Hejazi, Concord, NC (US); Rebecca H. Reynolds, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 714 days.

(21) Appl. No.: 16/408,942

(22) Filed: May 10, 2019

(65) Prior Publication Data

US 2020/0352256 A1  Nov. 12, 2020

(51) Int. Cl.
*A61M 15/06* (2006.01)

(52) U.S. Cl.
CPC ................... *A61M 15/06* (2013.01)

(58) Field of Classification Search
CPC ... A61M 15/06; A61M 11/042; A24F 47/008; A24F 47/002; A24F 40/10; A24F 40/42; A24F 40/40
See application file for complete search history.

(56) References Cited

U.S. PATENT DOCUMENTS

| | | |
|---|---|---|
| 2,057,353 A | 10/1936 | Whittemore, Jr. |
| 2,104,266 A | 1/1938 | McCormick |
| 3,200,819 A | 8/1965 | Gilbert |
| 4,922,901 A | 5/1990 | Brooks et al. |
| 5,060,671 A | 10/1991 | Counts et al. |
| 5,093,894 A | 3/1992 | Deevi et al. |
| 5,261,424 A | 11/1993 | Sprinkel, Jr. |
| 5,388,574 A | 2/1995 | Ingebrethsen et al. |
| 5,530,225 A | 6/1996 | Hajaligol |
| 5,687,746 A | 11/1997 | Rose et al. |
| 5,726,421 A | 3/1998 | Fleischhauer et al. |
| 5,865,185 A | 2/1999 | Collins et al. |
| 5,894,841 A | 4/1999 | Voges |

(Continued)

FOREIGN PATENT DOCUMENTS

| | | |
|---|---|---|
| CN | 1541577 | 11/2004 |
| CN | 2719043 | 8/2005 |

(Continued)

*Primary Examiner* — Marcus E Harcum
(74) *Attorney, Agent, or Firm* — Womble Bond Dickinson (US) LLP

(57) ABSTRACT

The present disclosure relates to a flavor delivery article, a cartridge, and/or an aerosol delivery device that includes such flavor delivery article or a component thereof. The flavor delivery article includes a flavor substrate that can be formed of a porous material optionally having a graded porosity across at least a portion thereof. The flavor substrate further includes a flavor material retained thereby. The flavor substrate may be positioned within an outer shell of the flavor delivery article, and the flavor delivery article may be positioned anywhere within an aerosol delivery device (or a mouthpiece or a cartridge of an aerosol delivery device) wherein the flavor substrate retaining the flavor material may be contacted by a gaseous stream, such as a vapor stream and/or aerosol stream formed in the aerosol delivery device so that the flavor material may become entrained in the vapor stream and/or aerosol stream.

23 Claims, 5 Drawing Sheets

(56) References Cited

U.S. PATENT DOCUMENTS

| | | | |
|---|---|---|---|
| 6,125,853 A | 10/2000 | Susa et al. | |
| 6,155,268 A | 12/2000 | Takeuchi | |
| 7,117,867 B2 | 10/2006 | Cox et al. | |
| 7,832,410 B2 | 11/2010 | Hon | |
| 8,066,011 B2* | 11/2011 | Clark | A24D 3/048 |
| | | | 131/337 |
| 8,314,591 B2 | 11/2012 | Terry et al. | |
| 8,365,742 B2 | 2/2013 | Hon | |
| 8,499,766 B1 | 8/2013 | Newton | |
| 2005/0016550 A1 | 1/2005 | Katase | |
| 2006/0196518 A1 | 9/2006 | Hon | |
| 2008/0092912 A1 | 4/2008 | Robinson et al. | |
| 2009/0095311 A1* | 4/2009 | Han | H01M 50/213 |
| | | | 131/194 |
| 2009/0126745 A1 | 5/2009 | Hon | |
| 2009/0188490 A1 | 7/2009 | Hon | |
| 2009/0272379 A1 | 11/2009 | Thorens et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0290248 A1 | 12/2011 | Schennum | |
| 2012/0111347 A1 | 5/2012 | Hon | |
| 2012/0260927 A1 | 10/2012 | Liu | |
| 2012/0279512 A1 | 11/2012 | Hon | |
| 2013/0037041 A1 | 2/2013 | Worm et al. | |
| 2013/0056012 A1* | 3/2013 | Hearn | A24F 42/20 |
| | | | 131/273 |
| 2013/0056013 A1 | 3/2013 | Terry et al. | |
| 2013/0306084 A1 | 11/2013 | Flick | |
| 2014/0000638 A1 | 1/2014 | Sebastian et al. | |
| 2014/0060554 A1 | 3/2014 | Collett et al. | |
| 2014/0060555 A1 | 3/2014 | Chang et al. | |
| 2014/0060556 A1* | 3/2014 | Liu | A24F 40/44 |
| | | | 131/329 |
| 2014/0096781 A1 | 4/2014 | Sears et al. | |
| 2014/0096782 A1 | 4/2014 | Ampolini et al. | |
| 2014/0166029 A1 | 6/2014 | Weigensberg et al. | |
| 2014/0209105 A1 | 7/2014 | Sears et al. | |
| 2014/0253144 A1 | 9/2014 | Novak et al. | |
| 2014/0261408 A1* | 9/2014 | DePiano | H05B 3/04 |
| | | | 128/202.21 |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2015/0027469 A1* | 1/2015 | Tucker | A24D 3/061 |
| | | | 131/329 |
| 2016/0135506 A1* | 5/2016 | Sanchez | A24F 40/30 |
| | | | 131/329 |
| 2016/0143360 A1 | 5/2016 | Sanchez et al. | |
| 2017/0065000 A1 | 3/2017 | Sears et al. | |
| 2017/0265517 A1* | 9/2017 | Swede | A24F 40/485 |
| 2017/0280769 A1* | 10/2017 | Li | A24B 15/283 |
| 2018/0007966 A1* | 1/2018 | Li | A24F 40/42 |
| 2018/0132535 A1* | 5/2018 | Reevell | A24F 40/40 |
| 2018/0169355 A1* | 6/2018 | Reevell | A61M 15/003 |
| 2019/0124982 A1* | 5/2019 | Atkins | A61M 11/042 |

FOREIGN PATENT DOCUMENTS

| | | | | |
|---|---|---|---|---|
| CN | 201379072 | | 1/2010 | |
| CN | 108471807 A | * | 8/2018 | ............ A24F 40/30 |
| EP | 0 295 122 | | 12/1988 | |
| EP | 0 845 220 | | 6/1998 | |
| EP | 1 618 803 | | 1/2006 | |
| GB | 2469850 | | 11/2010 | |
| KR | 20180117614 A | * | 10/2018 | ............ A24F 40/42 |
| KR | 102273679 B1 | * | 7/2021 | ............ A24F 40/40 |
| WO | WO 2003/034847 | | 5/2003 | |
| WO | WO 2004/080216 | | 9/2004 | |
| WO | WO 2005/099494 | | 10/2005 | |
| WO | WO 2007/131449 | | 11/2007 | |
| WO | WO2018/114261 | | 6/2018 | |
| WO | WO-2018114312 A1 | * | 6/2018 | ............ A24F 40/30 |

\* cited by examiner

FLAVOR ARTICLE FOR AN AEROSOL DELIVERY DEVICE

FIELD OF THE DISCLOSURE

The present disclosure relates to aerosol delivery devices, and more particularly to an aerosol delivery device that include a reservoir and a vaporizing assembly, which may utilize electrical power to heat an aerosol precursor composition for the production of an aerosol. The aerosol precursor composition, which may incorporate materials and/or components that may be made or derived from tobacco or otherwise incorporate tobacco, is heated by the vaporizing assembly to produce an inhalable substance for human consumption.

BACKGROUND

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference.

The goal of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Lorillard Technologies, Inc.; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™, MAXXQ™ PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R.J. Reynolds Vapor Company; Mistic Menthol product by Mistic Ecigs; and the Vype product by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™.

Certain existing embodiments of aerosol delivery devices include a control body (i.e., a power source assembly) and a cartridge (i.e., a reservoir housing). A power source (e.g., a battery) may be positioned in the control body, and an aerosol precursor composition may be retained and/or stored within the cartridge. It would be desirable to provide a cartridge capable of adding one or more flavors to the aerosol precursor composition as desired by the user.

SUMMARY OF THE DISCLOSURE

In various embodiments, the present disclosure provides a flavor article that can be included in, or combined with, an aerosol delivery device. The flavor article can incorporate at least one flavor substrate that is adapted to or configured to retain a flavor material that may be released therefrom for entrainment in a gaseous stream. As such, the flavor article is configured for inclusion within or attachment to an aerosol delivery device (or similar device) in any location therein where a flowing gaseous stream (e.g., an aerosol stream) may pass therealong.

The present disclosure can provide a variety of articles that are each adapted to or configured to provide a flavor. In some embodiments, the disclosure can relate to a flavor delivery article that can be adapted to or configured to be combined with a further article, such as a cartridge of an aerosol delivery device and/or a mouthpiece that is attachable to a cartridge of an aerosol delivery device. In further embodiments, the disclosure can relate to a flavor delivery mouthpiece that includes a flavor delivery article and that is adapted to or configured to be attached to a cartridge of an aerosol delivery device. In other embodiments, the present disclosure can relate to a cartridge of an aerosol delivery device. Such cartridge can include a flavor delivery article that can be included directly into the cartridge housing and/or can be include in a mouthpiece that is attached to the cartridge housing. In still further embodiments, the present disclosure can relate to an aerosol delivery device that includes a power unit and a cartridge. The power unit and cartridge can be provided in a single housing or can be provided in separate housings. The aerosol delivery device in particular can include a flavor delivery article combined therewith, such as being included in the cartridge and/or being included in a mouthpiece that is attached to the cartridge.

In one or more embodiments, a flavor delivery article according to the present disclosure can comprise: an outer shell extending along a longitudinal axis between a distal end including at least one opening and a proximal end including at least one opening, the outer shell defining a chamber therein; at least one elongated flavor substrate formed of a porous material and extending along a longitudinal axis between a first end and an opposing second end, the at least one elongated flavor substrate being positioned within the chamber of the outer shell such that the longitudinal axis of the at least one elongated substrate is substantially parallel with the longitudinal axis of the outer shell; and a flavor material retained by the elongated flavor substrate. In some embodiments, the flavor delivery article can be further characterized in relation to one or more of the following statements, which can be combined in any number or order.

The flavor delivery article further can comprise a film substantially circumscribing the at least one elongated flavor substrate.

The film can be formed of a polymeric material.

The polymeric material can be selected from the group consisting of polyesters, acetals, polycarbonates, celluloses, polyvinylidene fluoride (PVDF), low density polyethylene (LDPE), high density polyethylene (HDPE), polyvinylchloride (PVC), polytetrafluoroethylene (PTFE), polylactic acid (PLA), polyethylene terephthalate (PET), and combinations thereof.

The film can be formed of a material selected from the group consisting of paper foil, filter paper, ceramics, aluminum, and combinations thereof.

The film can have a thickness of about 2 microns to about 500 microns.

The at least one elongated flavor substrate can have a graded porosity across a wall thickness thereof.

The porous material forming the at least one elongated flavor substrate can be a polymeric material.

The polymeric material can be selected from the group consisting of polyethersulfone, polypropylene, polyethylene, polyester, nylon, polylactic acid (PLA), cellulose nitrate, regenerated cellulose, cellulose acetate, silica, cotton, and combinations thereof.

One or more of the following conditions can be met: the at least one elongated flavor substrate can be in the form of a pleated sheet; the at least one elongated flavor substrate can be in the form of a gathered sheet; the at least one elongated flavor substrate can be in the form of a rolled sheet; the at least one elongated flavor substrate can comprise one or more rods; the at least one elongated flavor substrate can comprise one or more tubes.

The flavor delivery article further can comprise a mouthpiece engaging the proximal end of the outer shell.

At least a portion of the outer shell can be shaped and dimensioned for insertion into a cartridge of an aerosol delivery device.

In some embodiments, the present disclosure can provide a cartridge for an aerosol delivery device. For example, the cartridge can comprise: a cartridge housing having a mouthend; a reservoir including an aerosol precursor composition; a heater adapted to vaporize the aerosol precursor composition; and a flavor delivery article as otherwise described herein engaged with the cartridge such that at least the distal end of the outer shell is engaged with the mouthend of the cartridge housing.

The cartridge further can comprise a liquid transport element configured for transport of the aerosol precursor composition between a reservoir and the heater.

The reservoir can include a fibrous material.

The reservoir can be a tank.

In some embodiments, the present disclosure can provide an aerosol delivery device. For example, the aerosol deliver device can comprise: a power unit housing including a power source and a controller; and a cartridge as otherwise described herein.

In some embodiments, the present disclosure can provide a cartridge for an aerosol delivery device. For example, the cartridge can comprise: a cartridge housing having a mouthend; a reservoir including an aerosol precursor composition; a heater adapted to vaporize the aerosol precursor composition; and a flavor delivery article comprising: at least one elongated flavor substrate formed of a porous material and extending along a longitudinal axis between a first end and an opposing second end; a flavor material retained by the elongated flavor substrate unit; and a film substantially circumscribing the at least one elongated flavor substrate.

The cartridge further can comprise an air entry and an airflow passage through the cartridge.

The heater and the flavor delivery article can be both positioned substantially within the airflow passage.

The flavor delivery article can be positioned in the airflow passage downstream from the heater.

The flavor delivery article can be positioned in a mouthpiece attached to the mouthend of the cartridge housing.

The cartridge can be adapted or configured such that one or more of the following conditions can be met: the at least one elongated flavor substrate can be in the form of a pleated sheet; the at least one elongated flavor substrate can be in the form of a gathered sheet; the at least one elongated flavor substrate can be in the form of a rolled sheet; the at least one elongated flavor substrate can comprise one or more rods; the at least one elongated flavor substrate can comprise one or more tubes.

BRIEF DESCRIPTION OF THE FIGURES

In order to assist the understanding of aspects of the disclosure, reference will now be made to the appended drawings, which are not necessarily drawn to scale and in which like reference numerals refer to like elements. The drawings are exemplary only, and should not be construed as limiting the disclosure.

DETAILED DESCRIPTION

Figure 1A:
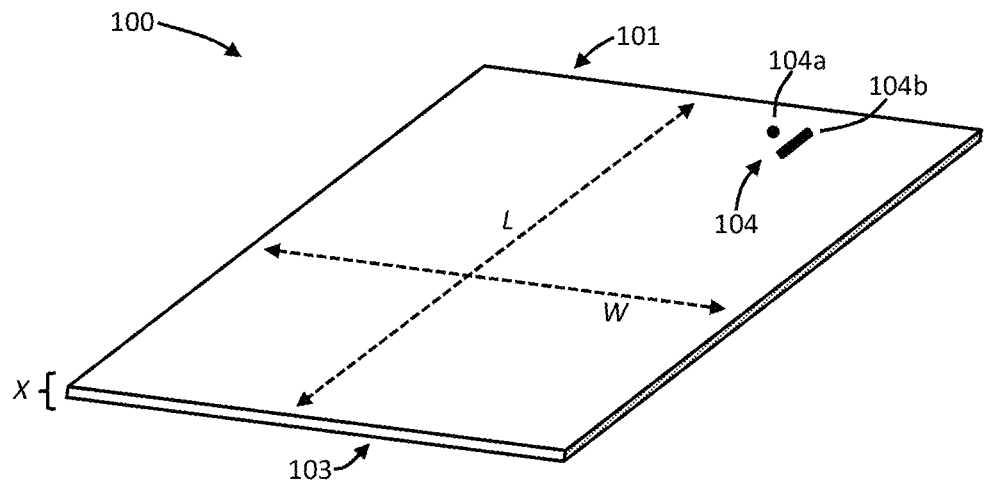
FIG. 1A is a perspective view of an example embodiment of a flavor substrate configured in a substantially sheet-like form according to the present disclosure.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of flavor articles that are adapted to or configured to provide a flavor to a passing vapor or aerosol stream. The flavor articles are particularly suited for combination with aerosol delivery devices. The aerosol delivery devices may use electrical energy to heat a material to form an inhalable substance; such articles may be sufficiently compact to be considered "hand-held" devices. An aerosol delivery devices may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery devices may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device, although in other implementations the aerosol may not be visible. In some implementations, aerosol delivery devices may incorporate tobacco and/or components derived from tobacco. As such, the aerosol delivery devices can be characterized as an electronic smoking article such as an electronic cigarette or "e-cigarette."

While the flavor articles are generally described herein in terms of implementations associated with aerosol delivery devices such as so-called "e-cigarettes," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Devices incorporating flavor articles according to the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, devices incorporating flavor articles of the present disclosure may be subjected to many of the physical actions employed by an individual in using a traditional type of smoking article (e.g., a cigarette, cigar or pipe that is employed by lighting and inhaling tobacco). For example, the user of a device of the present disclosure can hold that article much like a traditional type of smoking article, draw on one end of that article for inhalation of aerosol produced by that article, take puffs at selected intervals of time, etc.

A flavor article according to the present disclosure can, in one or more embodiments, comprise at least one elongated flavor substrate that is formed of a porous material. The flavor substrate can be adapted to or configured to extend along a longitudinal axis between a first end and an opposing second end and, as such, can have at least a longitudinal dimension or a length. The flavor substrate can vary in shape, as further discussed below, and thus can include further dimensions, such as thickness and/or width. Non-limiting examples of flavor substrates are shown in FIG. 1A, FIG. 1B, and FIG. 1C.

As seen in FIG. 1A, the flavor substrate 100 extends along a longitudinal axis L between a first end 101 and a second end 103 and has a width W that extends along an axis that is perpendicular to the longitudinal axis L and a thickness X. As such, the flavor substrate 100 can be substantially in the form of a sheet having a length (L) of about 0.2 cm to about 5 cm, about 0.3 cm to about 3 cm, about 0.4 cm to about 2.5 cm, or about 0.5 cm to about 2 cm. The flavor substrate likewise can have a width (W) of about 10% of the length to about 4000% of the length, about 20% of the length to about 2000% of the length, or about 50% of the length to about 1000% of the length. The thickness (X) can be about 5 microns to about 500 microns, about 10 microns to about 400 microns, or about 20 microns to about 300 microns. A flavor substrate 100 substantially in the form of a sheet can thus be adapted to or configured to be substantially flat. If desired, a flavor substrate 100 formed as a flat sheet can be embossed and/or include a plurality of perforations 104 therethrough. Perforations may be substantially round (see perforation 104*a*) or may be elongated (e.g., in the form of slits)—see perforation 104*b*.

Figure 1B:
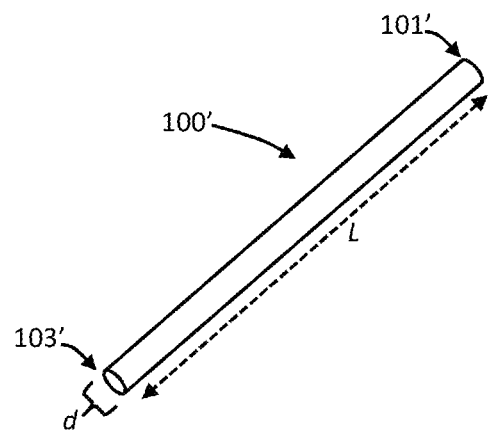
FIG. 1B is a perspective view of an example embodiment of a flavor substrate configured in a substantially rod-like form according to the present disclosure.

As seen in FIG. 1B, the flavor substrate 100' again extends along a longitudinal axis L between a first end 101' and a second end 103' and is substantially in the form of a rod having a diameter d. The flavor substrate 101' in the form of a rod can have a length (L) of about 0.2 cm to about 5 cm, about 0.3 cm to about 3 cm, about 0.4 cm to about 2.5 cm, or about 0.5 cm to about 2 cm and can have a diameter of about 1 micron to about 2,000 microns, about 5 microns to about 1,500 microns, or about 10 microns to about 1,000 microns.

Figure 1C:
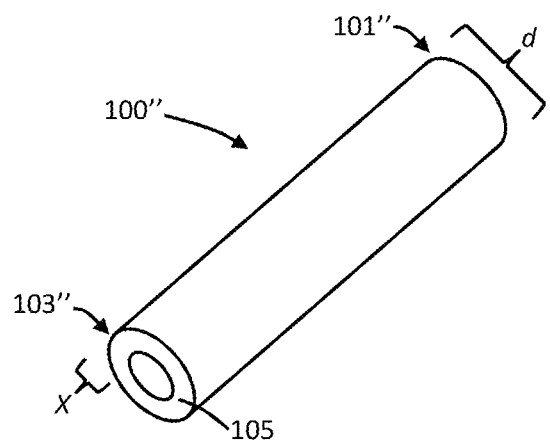
FIG. 1C is a perspective view of an example embodiment of a flavor substrate configured in a substantially tube-like form according to the present disclosure.

As seen in FIG. 1C, the flavor substrate 100" again extends along a longitudinal axis L between a first end 101" and a second end 103" and is substantially in the form of a hollow tube having a diameter d. The flavor substrate 101" in the form of a tube can have a length (L) of about 0.2 cm to about 5 cm, about 0.3 cm to about 3 cm, about 0.4 cm to about 2.5 cm, or about 0.5 cm to about 2 cm and can have a diameter of about 0.5 mm to about 25 mm, about 1 mm to about 20 mm, or about 2 mm to about 15 mm. The tube can have a substantially continuous wall 105 that can vary in thickness X along the longitudinal axis of the flavor substrate 100". In some embodiments, the thickness X of the substantially continuous wall 105 is preferably substantially uniform along the longitudinal axis of the flavor substrate 100". The substantially continuous wall 105, for example, can have an average thickness X of about 0.01 mm to about 5 mm, about 0.1 mm to about 4 mm, or about 0.2 mm to about 2 mm. Wall thickness may be substantially uniform (e.g., varying by no more than about 15%, no more than about 10%, no more than about 5%, or no more than about 2% along substantially the entire length of the tube. In some embodiments, wall thickness may vary along the length of the tube.

The flavor substrate in the form of a tube or rod may take on a variety of shapes and may have, for example, a cross-sectional shape, such as a circle, square, rectangle, oval, triangle, polygon, or the like. Although illustrated as having a substantially continuous diameter or thickness, in some embodiments, the diameter and/or thickness of the flavor substrate (or a wall of the flavor substrate) can vary along the length thereof. For example, the diameter and/or thickness may increase from the first end (101, 101', 101") to the second end (103, 103', 103") so that a diameter and/or thickness of the second end is greater than a diameter and/or thickness of the first end by about 1% to about 600%, about 25% to about 500%, about 50% to about 400%, or about 75% to about 250%. Alternatively, the diameter and/or thickness may decrease from the first end (101, 101', 101") to the second end (103, 103', 103") so that a diameter and/or thickness of the second end is greater than the diameter of the first end by about 1% to about 600%, about 25% to about 500%, about 50% to about 400%, or about 75% to about 250%.

The flavor substrate (100, 100', 100") can be formed of a porous material that is adapted to or configured to permit flavor liquid to be stored within pores present in the porous material and also permit the flavor liquid to diffuse away from the flavor substrate to be entrained in a passing gaseous stream. The flavor substrate (100, 100', 100") can be adapted to or configured to absorb the flavor liquid, retain the flavor liquid, and release the flavor liquid as particles or droplets that can be entrained by a gaseous stream passing along the exterior surface thereof. The flavor substrate (100, 100', 100") thus may be formed of a nanoporous, microporous, and/or macroporous material. In some embodiments, porosity of the flavor substrate (100, 100', 100") can be substantially uniform across a thickness of the substrate (e.g., pore size varying by no more than about 15%, no more than about 10%, no more than about 5%, or no more than about 2% across the thickness of the substrate).

In some embodiments, the flavor substrate (100, 100', 100") may be formed at least in part from one or more polymeric materials, such as polyethersulfone, polypropylene, polyethylene, polyester (e.g., polyethylene terephthalate and polypropylene terephthalate), nylon, polylactic acid (PLA), cellulosic materials (e.g., cellulose nitrate, regenerated cellulose, cellulose acetate), silica, cotton, and combinations thereof. Biodegradable polymers likewise may be utilized for this purpose. For example, the flavor substrate (100, 100', 100") may be formed at least partially from fibers formed from any of the foregoing materials alone or in one or more combinations. Likewise, any one or more of the foregoing materials may be expressly excluded from use in one or more embodiments of the disclosure.

In some embodiments, the flavor substrate (100, 100', 100") may be formed from one or more layers (e.g., one layer, two layers, three layers, four layers, or more layers), and separate layers may be formed of different materials. When a plurality of layers is used, the layers can be prepared using coextrusion or other known techniques in the art.

In some embodiments, the flavor substrate (100, 100', 100") can be adapted to or configured to exhibit a graded porosity across a thickness thereof (or a thickness of a wall thereof). As used herein, a graded material or functionally graded material is understood to be a material wherein the composition, the microstructure, or both are locally varied so that a certain variation of the local material properties is achieved. Functionally graded materials are particularly useful for forming a flavor substrate or a wall thereof or a portion thereof as described herein in that they can be structurally engineered to allow for discrete or continual variations in the molecular modeling of the wall. This allows for substrates (or portions thereof) with varying capillary action across the thickness thereof. The flavor substrate particularly can be defined as being functionally graded in that the average pore size can vary across the thickness of the flavor substrate (or a portion thereof). In some embodiments, the material(s) forming the flavor substrate are functionally graded such that the average pore size increases from an inner layer or section of the flavor substrate to an outer layer or section of the flavor substrate. As such, the flavor substrate can be functionally graded in average pore size from the inner layer or section of the flavor substrate to the outer layer or section of the flavor substrate such that the average pore size of the inner layer or section of the flavor substrate is smaller than the average pore size of the outer layer or section of the flavor substrate. In further embodiments, the material(s) forming the flavor substrate are functionally graded such that the average pore size decreases from an inner layer or section of the flavor substrate to an outer layer or section of the flavor substrate. As such, the flavor substrate can be functionally graded in average pore size from the inner layer or section of the flavor substrate to the outer layer or section of the flavor substrate such that the average pore size of the inner layer or section of the flavor substrate is greater than the average pore size of the outer layer or section of the flavor substrate.

Figure 2:
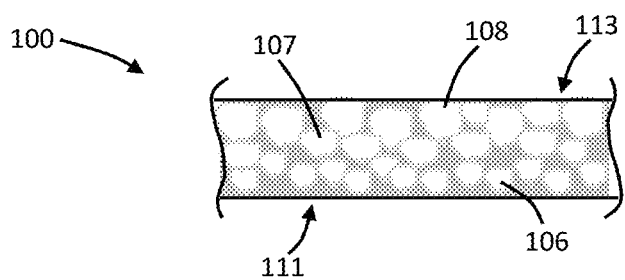
FIG. 2 is an illustration of a portion of a flavor substrate according to an example embodiment of the present disclosure showing a graded porosity.

The relatively small pores can have a first average size, and the relatively large pores can have a second average size. In further embodiments, pores having an intermediate average size that is between the first average size and the second average size can also be present. The intermediate average size can be referred to as a third average size. In one or more embodiments, the first average size for the relatively small pores can be about 1 nm to about 5 µm, about 100 nm to about 3 µm, about 250 nm to about 2 µm, or about 500 nm to about 1 µm. In further embodiments, the second average size for the relatively large pores can be about 0.1 µm to about 30 µm, about 0.5 µm to about 30 µm, about 1 µm to about 20 µm, or about 3 µm to about 10 µm. Pores having an intermediate average size can be between the ranges noted above. Pore size may vary across a thickness of at least a portion of the flavor substrate (or a wall thereof) and/or may vary along a length and/or width of the flavor substrate. As an example, FIG. 2 shows a partial cross-section of the flavor substrate 100 from FIG. 1A. As seen therein, pores 106 proximate a first surface 111 of the flavor substrate 100 have a first, relatively small average pore size, pores 108 proximate a second surface 113 of the flavor substrate have a second, relatively large average pore size, and pores 107 substantially between the first surface and the second surface have a third, intermediate average pore size.

Figure 3A:
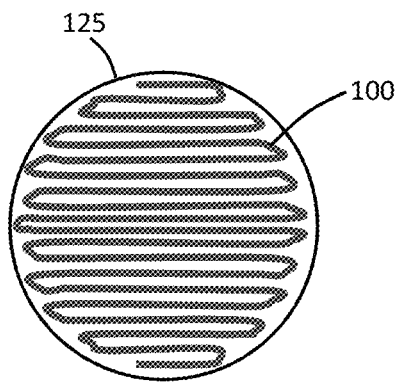
FIG. 3A is a partial cross-sectional view of an example embodiment of flavor substrate that is at least partially circumscribed by an outer film, wherein the flavor substrate is configured as a pleated sheet.
Figure 3B:
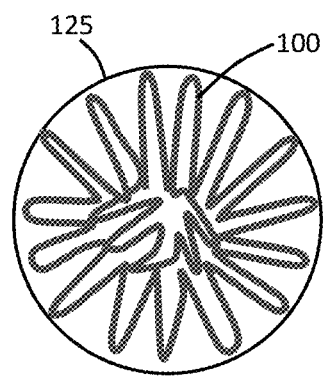
FIG. 3B is a partial cross-sectional view of an example embodiment of flavor substrate that is at least partially circumscribed by an outer film, wherein the flavor substrate is configured as a gathered sheet.
Figure 3C:
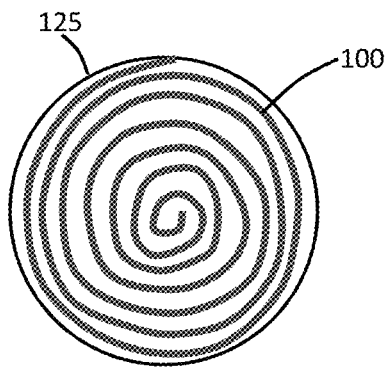
FIG. 3C is a partial cross-sectional view of an example embodiment of flavor substrate that is at least partially circumscribed by an outer film, wherein the flavor substrate is configured as a rolled sheet.

The flavor substrate (100, 100', 100") can be configured so that a substantially large surface area is provided for passage of flavor liquid from the flavor substrate to a gaseous stream passing along the longitudinal length of the flavor substrate. This can be achieved by providing the flavor substrate in a specified configuration and/or by providing a plurality of flavor substrates in combination. FIG. 3A, for example illustrates a flavor substrate 100 that is in a folded or pleated configuration. An optional, outer film 125 is also shown. As a further example, FIG. 3B illustrates a flavor substrate 100 that is in a gathered configuration and surrounded by an optional outer film 125. As another example, FIG. 3C illustrates a flavor substrate 100 that is in a rolled configuration and surrounded by an optional outer film 125. A flavor substrate 100 substantially in the form of a sheet can be provided in any one or more of the foregoing configuration as well as further, similar configurations wherein the sheet is aggregated in a manner to maximize the available surface area across which an aerosol or similar fluid may flow. Although only a single sheet is illustrated as being aggregated (e.g., folded, gathered, or rolled), it is understood that a plurality of sheets (e.g., two, three, four, five, or even more) may be combined. Moreover, when a plurality of sheets is used, two or more individual sheets may be formed of different materials and/or be adapted to or configured to provide different properties. For example, two sheets (or more sheets) adapted to provide two or more different flavors may be utilized to provide a desired flavor combination.

Figure 3D:
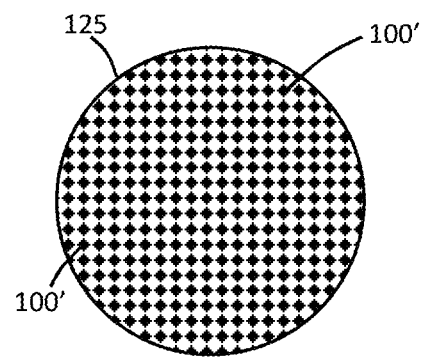
FIG. 3D is a partial cross-sectional view of an example embodiment of flavor substrate that is at least partially circumscribed by an outer film, wherein the flavor substrate is configured as a plurality of rods.
Figure 3E:
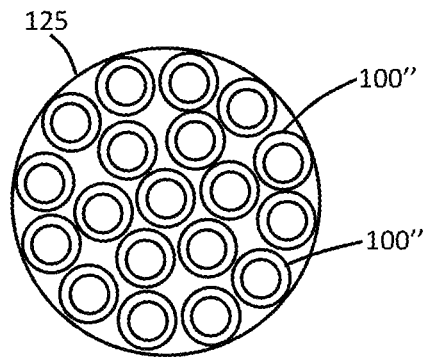
FIG. 3E is a partial cross-sectional view of an example embodiment of flavor substrate that is at least partially circumscribed by an outer film, wherein the flavor substrate is configured as a plurality of tubes.
Figure 3F:
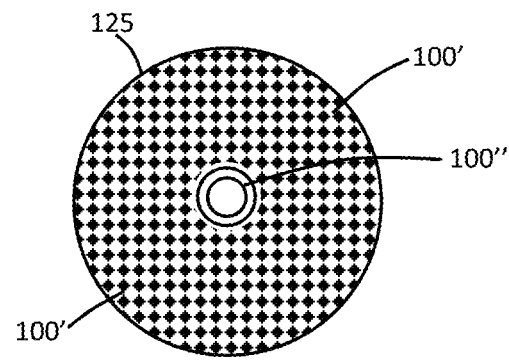
FIG. 3F is a partial cross-sectional view of an example embodiment of flavor substrate that is at least partially circumscribed by an outer film, wherein the flavor substrate is configured as a combination of a tube and a plurality of rods.
Figure 3G:
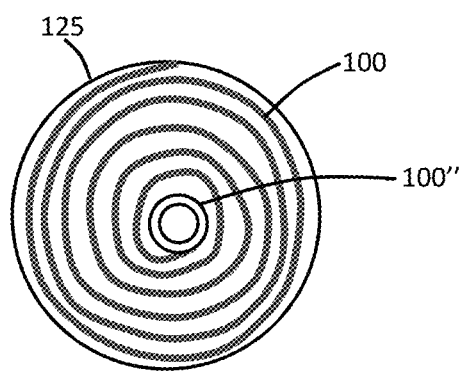
FIG. 3G is a partial cross-sectional view of an example embodiment of flavor substrate that is at least partially circumscribed by an outer film, wherein the flavor substrate is configured as a combination of a rolled sheet and a plurality of tubes.

As yet a further example, FIG. 3D illustrates a plurality of flavor substrates 100' that are provided in the form of rods having a substantially square cross-section (although any shaped cross-section is envisioned) and being surrounded by an optional outer film 125. The plurality of rods is shown in a grid-like pattern, but any packing style may be utilized. As still another example, FIG. 3E illustrates a plurality of flavor substrates 100" that are provided in the form of tubes having a substantially round cross-section (although any shaped cross-section is envisioned) and being surrounded by an optional outer film 125. The plurality of tubes may be provided with any packing style desired. As yet another example, FIG. 3F illustrates the use of two different types of flavor substrates. A plurality of flavor substrates 100' in the form of rods are included along with a single flavor substrate 100" in the form of a tube, all being surrounded by an optional outer film 125. Again, the rods and tubes may have any desired cross-section and may be provided in any desired number. In particular, although only a single flavor substrate tube 100" is illustrated, it is understood that a plurality of flavor substrate rods 100' may be combined with a plurality of flavor substrate tubes 100". As yet a further example, FIG. 3G also illustrates the use of two different types of flavor substrates. A flavor substrate 100 in the form of a sheet is included with a single flavor substrate 100" in the form of a tube, all being surrounded by an optional outer film 125. Again, the sheet and tube may have any desired cross-section and may be provided in any desired number (e.g., a single sheet with a plurality of tubes, a single tube with a plurality of sheets, or a plurality of sheets with a plurality of tubes). Likewise, any number of flavor substrate rod(s) 100' and/or flavor substrate tube(s) 100" may be combined with any number of flavor substrate sheet(s) 100 that may be pleated, gathered, or wrapped.

The outer film 125 may be excluded in one or more embodiments or the outer film may be expressly included. In particular, it can be useful to provide the flavor substrate (100, 100', 100") surrounded by the outer film 125 to improve manufacturability of the flavor device and to allow for ease of replacement of used flavor substrates in a further device, as otherwise described herein. The outer film 125 can be provided so that it is substantially circumscribing the flavor substrate(s) that are used. Preferably, the outer film, when used, is present substantially along the complete longitudinal length of the flavor substrate. It is understood, however, that the outer film may be present only along a partial length of the flavor substrate, such as only along about a mid-section of the longitudinal length of the flavor substrate or only proximate one end of the flavor substrate. As non-limiting examples, the outer film 125 can be in the form of a sheet that can be substantially wrapped around the substrate or combination of substrates, and the wrapped sheet can be glued, stitched, welded, or otherwise attached to one or more of the substrate(s) and/or to itself. As a further example, the outer film 125 can be provided substantially in the form of a tube, straw, or the like, and can be slid around the substrate(s) or the substrate(s) may be positioned into the tube. In one or more embodiments, the outer film can be formed of a polymeric material. As non-limiting examples, suitable materials for forming the outer film can include polyesters, acetals, polycarbonates, celluloses, polyvinylidene fluoride (PVDF), low density polyethylene (LDPE), high density polyethylene (HDPE), polyvinylchloride (PVC), polytetrafluoroethylene (PTFE), polylactic acid (PLA) polyethylene terephthalate (PET), and combinations thereof. In some embodiments, the outer film particularly may be formed from a biodegradable material. In other examples, the outer film may be formed of different types of materials than a polymeric material. For example, in some embodiments, the outer film can be formed of paper foil, filter paper, ceramics, aluminum, or any combinations thereof. Likewise, combinations of polymeric materials and non-polymeric materials may also be used. The outer film can vary in thickness, and the thickness can be substantially constant along the complete length thereof or may vary. In some embodiments, the outer film can have a thickness of about 2 microns to about 500 microns, about 5 microns to about 250 microns, or about 10 microns to about 100 microns. In further embodiments, a substantially thicker material may be used. For example, the outer film can have a thickness of about 50 microns to about 1,000 microns, about 75 microns to about 800 microns, or about 100 microns to about 750 microns.

As noted above, a flavor material can be retained by the flavor substrate. The flavor material may be, for example, adsorbed and/or absorbed by the flavor substrate. In particular, the flavor material may be at least partially retained within the pores of the flavor substrate. The retaining of the flavor material by the flavor substrate is preferably a releasable relationship so that the flavor material may be released from the flavor substrate to be entrained into a passing gaseous stream.

In some embodiments, the flavor material then can include one or more flavorants. As used herein, reference to a "flavorant" is intended to refer to compounds or components that can be present in a flavor material (e.g., a flavor liquid) and that can be delivered to a user and which impart a sensory experience in terms of taste and/or aroma. Exemplary flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos, as well as any combination of the foregoing flavors. Syrups, such as high fructose corn syrup, also can be employed. Exemplary plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. For other examples of flavoring materials that may be suitable for the products disclosed, see, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference. It should be noted that reference to a flavorant should not be limited to any single flavorant as described above, and may, in fact, represent a combination of one or more flavorants.

A flavor substrate combined with a flavor material can be particularly suitable according to embodiments of the present disclosure for combination with other articles, such as aerosol delivery devices in a variety of forms. As such, the flavor substrate and flavor material can be provided in a form whereby the flavor substrate may be easily combinable with such further devices. In some embodiments, the flavor substrate may form part of a flavor delivery article that can further include an outer shell that is adapted to or configured to retain the flavor substrate.

Figure 4:
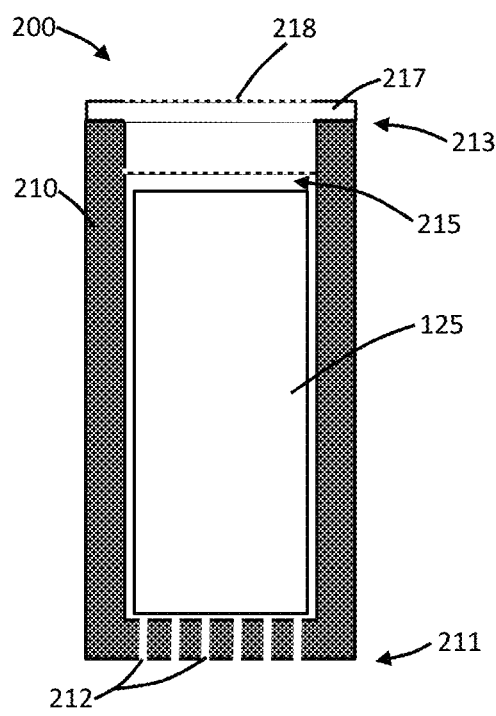
FIG. 4 is a partial cross-sectional view of an example embodiment of a flavor delivery article according to the present disclosure.

As seen in FIG. 4, a flavor delivery article 200 according to an example embodiment can comprise an outer shell 210 extending along a longitudinal axis between a distal end 211 including at least one opening and a proximal end 213 including at least one opening, the outer shell defining a chamber 215 therein. In the embodiment of FIG. 4, the distal end 211 includes a plurality of openings 212 in for the form of perforations through the outer shell 210, and the proximal end 213 includes a single opening in which a cap 217 is positioned, the cap including a series of perforations 218. A flavor substrate (100, 100', 100'') circumscribed with an outer film 125 is positioned within the chamber 215, although it is understood that the flavor substrate may be positioned within the chamber without the inclusion of an outer film. Preferably, at least one elongated flavor substrate (100, 100', 100'') is positioned within the chamber 215 of the outer shell 210 such that the longitudinal axis of the at least one elongated substrate is substantially parallel with the longitudinal axis of the outer shell. The so-formed flavor delivery article 200 may then be adapted for or configured for insertion into an aerosol delivery device or similar device so that vapor or aerosol formed in the delivery device may pass through the openings 212 in the outer shell 210 of the flavor delivery article 200, and flavor material retained by the flavor substrate (100, 100', 100'') may become entrained in the vapor or aerosol, which then exits the flavor delivery article through the perforations 218 in the cap 217 of the flavor delivery article.

Figure 5:
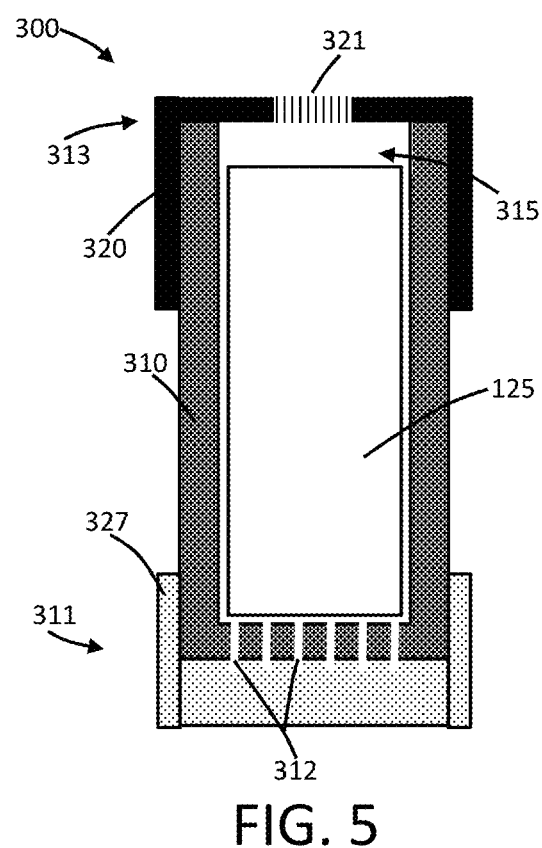
FIG. 5 is a partial cross-sectional view of a further example embodiment of a flavor delivery article according to the present disclosure.

A further example embodiment a flavor delivery article 300 is shown in FIG. 5, and such flavor delivery article can be particularly adapted to or configured to be added to a mouthend of an aerosol delivery device or similar device. Referring to FIG. 5, a flavor delivery article 300 according to an example embodiment can comprise an outer shell 310 extending along a longitudinal axis between a distal end 311 including at least one opening and a proximal end 313 including at least one opening, the outer shell defining a chamber 315 therein. In the embodiment of FIG. 5, the distal end 311 includes a plurality of openings 312 in for the form of perforations through the outer shell 310, and the proximal end 313 includes a single opening that is covered with a mouthpiece 320 that extends along the proximal end of the outer shell and also extends down the longitudinal length of the outer shell toward the distal end thereof, such as a distance of about 5% to about 90%, about 10% to about 75%, or about 15% to about 50% of the total longitudinal length of the outer shell. The mouthpiece 320 can be formed of any suitable material and can include a mouth opening 321 adapted for or configured for passage of vapor or aerosol therethrough. The mouth opening 321 can comprise a plurality of apertures or may include a mesh, screen, or similar element suitable for retaining the flavor substrate (100, 100', 100") therein. The mouthpiece 320 may be removable and/or replaceable.

As seen in FIG. 5, the flavor substrate circumscribed with an outer film 125 is positioned within the chamber 315, although it is understood that the flavor substrate may be positioned within the chamber without the inclusion of an outer film. Preferably, at least one elongated flavor substrate (100, 100', 100") is positioned within the chamber 315 of the outer shell 310 such that the longitudinal axis of the at least one elongated substrate is substantially parallel with the longitudinal axis of the outer shell. The so-formed flavor delivery article 200 may then be adapted for or configured for combination with an aerosol delivery device or similar device so that vapor or aerosol formed in the delivery device may pass through the openings 312 in the outer shell 310 of the flavor delivery article 300, and flavor material retained by the flavor substrate (100, 100', 100") may become entrained in the vapor or aerosol, which then exits the flavor delivery article through the mouth opening 321 in the mouthpiece 320 of the flavor delivery article. The flavor delivery article 300 thus may be partially inserted into an aerosol delivery device or similar article. In particular, at least a portion of the outer shell 310 can be shaped and dimensioned for insertion into a cartridge of an aerosol delivery device or similar article. Alternatively, the flavor delivery article 300 may include a skirt 327 around the distal end 311 of the outer shell 310 adapted to or configured to allow the flavor delivery article to slide around a mouth end of an aerosol delivery device or similar article. Such skirt may optionally be present with the flavor delivery article 200 of FIG. 4.

The flavor material may be combined with the flavor substrate (100, 100', 100") before or after the flavor substrate is circumscribed by the optional outer film. Likewise, the flavor material may be combined with the flavor substrate (100, 100', 100") before or after the flavor substrate is added to an outer shell (210, 310) to form a flavor delivery article. For example, a flavor substrate already positioned within an outer shell may have the flavor material in the form of a liquid injected therein via a syringe.

The flavor delivery article (200, 300) is beneficially useful for imparting a desired flavoring effect to a gaseous stream. As such, the flavor delivery article (200, 300) can be combined with any type of device that is configured for providing a flow of a gaseous stream. This can include, in example embodiments, an aerosol delivery device such further described herein or having different configurations of parts but intended to provide the same function of acting on an aerosol precursor liquid to form a vapor that can be entrained in a passing air stream and thus form an aerosol.

Figure 6:
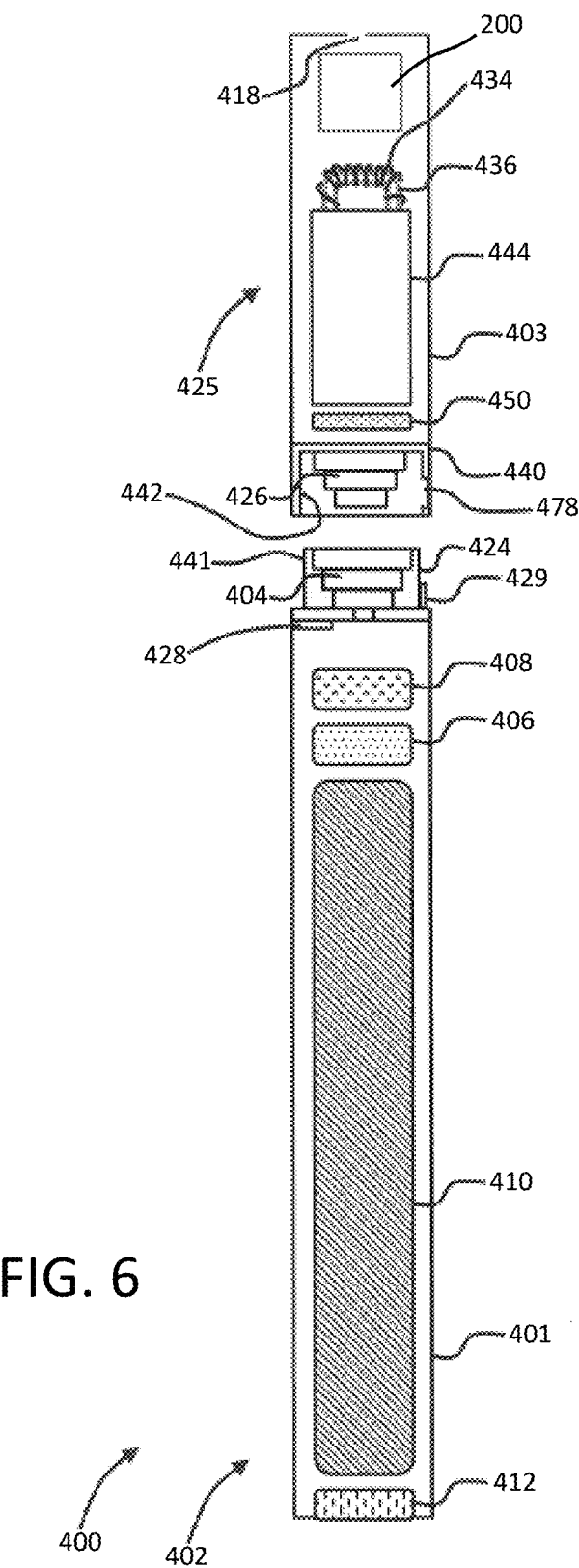
FIG. 6 is a partial cross-sectional view of an aerosol delivery device including a flavor delivery article according to the present disclosure.

For example, referring to FIG. 6, when a cartridge 404 is engaged with a power unit, a user drawing through the opening 428 at the mouthend of the cartridge will cause air to enter through the air entry 418. The air may flow through and/or around the reservoir 444 and entrain vapor that is formed by heating of aerosol precursor composition in the liquid transport element 436 by the heater 434 and thus form an aerosol that exits through the opening 428. There thus can be one or more airflow passages through the aerosol delivery device. As just described, the heater 434 can be positioned substantially within the airflow passage so that formed vapor is efficiently made available for entrainment in the air flowing through the cartridge 404.

In some embodiments, a flavor delivery article (200, 300) as described herein can be positioned substantially within the airflow passage. For example, in some embodiments, as illustrated in FIG. 6, the flavor delivery article 200 may be positioned within the cartridge 425 near a mouthend thereof. In further embodiments, the flavor delivery article 300 may be combined with a cartridge and function essentially as a mouthpiece for an aerosol delivery device. The flavor delivery article 300 including a mouthpiece 320 can include a flavor substrate positioned therein and, as such, the flavor delivery article that is so-formed can be adapted to or configured to be combined with another article, such as an aerosol delivery device. In one or more embodiments, the flavor delivery article (200, 300) may be provided as a stand-alone unit that is combinable with other devices as desired to add flavor to an unflavored aerosol or provide a further flavor to be mixed with the flavor already provided by the paired device.

Devices incorporating flavor articles of the present disclosure generally can include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped). Thus, an aerosol delivery device as described herein may take on any configuration desired.

In one implementation, all of the components of the aerosol delivery device are contained within one outer body, which may be defined as a housing or shell. Alternatively, an aerosol delivery device can comprise two or more shells that are joined and are separable. For example, an aerosol delivery device can comprise a control body or power unit including a shell containing one or more reusable components (e.g., a rechargeable battery and various electronics for controlling the operation of that article), and also can comprise a removably attached shell configured as a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure may comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance or inductive heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (which may itself contain one or more flavorants, medicaments, or other additives) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery and/or other electrical power source (e.g., a capacitor) to provide current flow sufficient to provide various functionalities to the aerosol delivery device, such as powering of a heater, powering of control systems, powering of indicators, and the like. The power source can take on various implementations. In one example, the power source is able to deliver sufficient power to rapidly heat the heating element to provide for aerosol formation and power the aerosol delivery device through use for a desired duration of time. The power source may be sized to fit conveniently within the aerosol delivery device so that the aerosol delivery device can be easily handled. Additionally, in one embodiment, a power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure as well as manufacturers, designers, and/or assignees of components and related technologies that may be employed in the aerosol delivery device of the present disclosure are described in U.S. patent application Ser. No. 15/222,615, filed Jul. 28, 2016, to Watson et al., which is incorporated herein by reference in its entirety.

One example embodiment of an aerosol delivery device 400 illustrating components that may be utilized in an aerosol delivery device according to the present disclosure is provided in FIG. 6. As seen in the cut-away view illustrated therein, the aerosol delivery device 400 can comprise a power unit 402 and a cartridge 404 that can be permanently or detachably aligned in a functioning relationship. Engagement of the power unit 402 and the cartridge 404 can be press fit (as illustrated), threaded, interference fit, magnetic, or the like. In particular, connection components, such as further described herein may be used. For example, the power unit may include a coupler that is adapted to engage a connector on the cartridge.

In specific embodiments, one or both of the power unit 402 and the cartridge 404 may be referred to as being disposable or as being reusable. For example, the power unit may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a power unit connector at an opposing end is disclosed in U.S. Pat. Pub. No. 2014/0261495 to Novak et al., which is incorporated herein by reference in its entirety. Further, in some embodiments the cartridge may comprise a single-use cartridge, as disclosed in U.S. Pat. No. 8,910,639 to Chang et al., which is incorporated herein by reference in its entirety.

As illustrated in FIG. 6, a power unit 402 can be formed of a power unit shell 401 that can include a control component 406 (e.g., a printed circuit board (PCB), an integrated circuit, a memory component, a microcontroller, or the like), a flow sensor 408, a battery 410, and an LED 412, and such components can be variably aligned. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference.

A cartridge 404 can be formed of a cartridge shell 403 enclosing the reservoir 444 that is in fluid communication with a liquid transport element 436 adapted to wick or otherwise transport an aerosol precursor composition stored in the reservoir housing to a heater 434. A liquid transport element can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus can be any material that contains an open pore network (i.e., a plurality of pores that are interconnected so that fluid may flow from one pore to another in a plurality of direction through the element).

Various embodiments of materials configured to produce heat when electrical current is applied therethrough may be employed to form the resistive heating element 434. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, graphite and graphite-based materials (e.g., carbon-based foams and yarns) and ceramics (e.g., positive or negative temperature coefficient ceramics). Various other implementations of a heating element likewise may be employed. For example, a metal mesh may be positioned around a cylindrical wick, or a ribbon-like metal mesh may be positioned on a ribbon-shaped or sheet-shaped wick. For example, a heating element may be configured to heat the aerosol precursor composition disposed within a liquid transport element via radiant heating, as described in U.S. Pat. App. Pub. No. 2017/0020193, filed Dec. 3, 2015, the content of which is incorporated herein by reference. In another implementation, the heating element may be configured to heat the aerosol precursor composition via inductive heating, as described in U.S. Pat. App. Pub. No. 2017/0127722, filed Nov. 6, 2015, the content of which is incorporated herein by reference. A variety of heater components may be used in the present aerosol delivery device. In various implementations, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference.

An opening 428 may be present in the cartridge shell 403 (e.g., at the mouthend) to allow for egress of formed aerosol from the cartridge 404. Such components are representative of the components that may be present in a cartridge and are not intended to limit the scope of cartridge components that are encompassed by the present disclosure.

The cartridge 404 also may include one or more electronic components 450, which may include an integrated circuit, a memory component, a sensor, or the like. The electronic component 450 may be adapted to communicate with the control component 406 and/or with an external device by wired or wireless means. The electronic component 450 may be positioned anywhere within the cartridge 404 or its base 440.

Although the control component 406 and the flow sensor 408 are illustrated separately, it is understood that the control component and the flow sensor may be combined as an electronic circuit board with the air flow sensor attached directly thereto. Further, the electronic circuit board may be positioned horizontally relative the illustration of FIG. 6 in that the electronic circuit board can be lengthwise parallel to the central axis of the power unit. In some embodiments, the air flow sensor may comprise its own circuit board or other base element to which it can be attached. In some embodiments, a flexible circuit board may be utilized. A flexible circuit board may be configured into a variety of shapes, include substantially tubular shapes.

The power unit 402 and the cartridge 404 may include components adapted to facilitate a fluid engagement therebetween. As illustrated in FIG. 6, the power unit 402 can include a coupler 424 having a cavity 425 therein. The cartridge 404 can include a base 440 adapted to engage the coupler 424 and can include a projection 441 adapted to fit within the cavity 425. Such engagement can facilitate a stable connection between the power unit 402 and the cartridge 404 as well as establish an electrical connection between the battery 410 and control component 406 in the power unit and the heater 434 in the cartridge. Further, the power unit shell 401 can include an air entry 418, which may be a notch in the shell where it connects to the coupler 424 that allows for passage of ambient air around the coupler and into the shell where it then passes through the cavity 425 of the coupler and into the cartridge through the projection 441.

A coupler and a base useful according to the present disclosure are described in U.S. Pat. Pub. No. 2014/0261495 to Novak et al., the disclosure of which is incorporated herein by reference in its entirety. For example, a coupler as seen in FIG. 6 may define an outer periphery 426 configured to mate with an inner periphery 442 of the base 440. In one embodiment the inner periphery of the base may define a radius that is substantially equal to, or slightly greater than, a radius of the outer periphery of the coupler. Further, the coupler 424 may define one or more protrusions 429 at the outer periphery 426 configured to engage one or more recesses 478 defined at the inner periphery of the base. However, various other embodiments of structures, shapes, and components may be employed to couple the base to the coupler. In some embodiments the connection between the base 440 of the cartridge 404 and the coupler 424 of the power unit 402 may be substantially permanent, whereas in other embodiments the connection therebetween may be releasable such that, for example, the power unit may be reused with one or more additional cartridges that may be disposable and/or refillable.

The aerosol delivery device 400 may be substantially rod-like or substantially tubular shaped or substantially cylindrically shaped in some embodiments. In other embodiments, further shapes and dimensions are encompassed—e.g., a rectangular or triangular cross-section, multifaceted shapes, or the like. In particular, the power unit 402 may be non-rod-like and may rather be substantially rectangular, round, or have some further shape. Likewise, the power unit 402 may be substantially larger than a power unit that would be expected to be substantially the size of a conventional cigarette.

The reservoir 444 illustrated in FIG. 6 can be a container (e.g., formed of walls substantially impermeable to the aerosol precursor composition) or can be a fibrous reservoir. Container walls can be flexible and can be collapsible. Container walls alternatively can be substantially rigid. A container reservoir may be referred to as a tank. Moreover, a fibrous material may be provided in at least a portion of a container. In exemplary embodiments, the reservoir 444 can comprise one or more layers of nonwoven fibers substantially formed into the shape of a tube encircling the interior of the cartridge shell 403. An aerosol precursor composition can be retained in the reservoir 444. Liquid components, for example, can be sorptively retained by the reservoir 444 (i.e., when the reservoir 444 includes a fibrous material). The reservoir 444 can be in fluid connection with a liquid transport element 436. The liquid transport element 436 can transport the aerosol precursor composition stored in the reservoir 444 via capillary action to the heating element 434 that is in the form of a metal wire coil in this embodiment. As such, the heating element 434 is in a heating arrangement with the liquid transport element 436.

In use, when a user draws on the article 400, airflow is detected by the sensor 408, the heating element 434 is activated, and the components for the aerosol precursor composition are vaporized by the heating element 434.

Drawing upon the mouthend of the article 400 causes ambient air to enter the air entry 418 and pass through the cavity 425 in the coupler 424 and the central opening in the projection 441 of the base 440. In the cartridge 404, the drawn air combines with the formed vapor to form an aerosol. The aerosol is whisked, aspirated, or otherwise drawn away from the heating element 434 and out the mouth opening 428 in the mouthend of the article 400.

An input element may be included with the aerosol delivery device. The input may be included to allow a user to control functions of the device and/or for output of information to a user. Any component or combination of components may be utilized as an input for controlling the function of the device. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference.

In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device can incorporate a sensor or detector for control of supply of electric power to the heat generation element when aerosol generation is desired (e.g., upon draw during use). As such, for example, there is provided a manner or method for turning off the power supply to the heat generation element when the aerosol delivery device is not be drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference.

The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pub. No. 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol and/or water), be employed in order to provide for the generation of a visible mainstream aerosol that in many regards resembles the appearance of tobacco smoke. In some embodiments, it can be preferred for the aerosol forming material to be provided in a sufficiently low viscosity to more readily intermix with the flavor provided from the present flavor delivery device. For example, in some embodiments, an aerosol precursor composition utilized with a flavor delivery device as described may include less than 70%, less than 65%, or less than 60% by weight of glycerin. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g. If desired, however, larger amounts of aerosol precursor composition may be used.

In some embodiments, the aerosol precursor may be substantially unflavored and/or may expressly exclude a dedicated flavorant. In this manner, an unflavored aerosol may be produced, and the produced aerosol may be subject to being flavored only by the presence of the flavor material in or on the flavor substrate (100, 100', 100"). Alternatively, the aerosol precursor may include a flavor, and the flavored aerosol that is produced from the aerosol precursor may be subject to being flavored additionally by the presence of the flavor material in or on the flavor substrate (100, 100', 100"). In this manner, unique flavor combinations can be provided. Likewise, the flavor substrate (100, 100', 100") can include a plurality of different flavors (e.g., two, three, four, or even more) that can be provided in desirable combinations to provide a desired flavoring effect to an aerosol.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article illustrated in FIG. 6 or as otherwise described above may be included in an aerosol delivery device according to the present disclosure. For example, a cartridge for an aerosol delivery device according to embodiments of the present disclosure can include a cartridge housing having a mouthend, a reservoir including an aerosol precursor composition, a heater adapted to vaporize the aerosol precursor composition, and a flavor delivery article as otherwise described herein engaged with the cartridge such that at least the distal end of the outer shell is engaged with the mouthend of the cartridge housing. For example, a flavor delivery article can be fully or completely inserted into a cartridge. As another example, a flavor delivery article can be partially inserted into a cartridge (e.g., the distal end of the outer shell of the flavor delivery article can be inserted into the cartridge). As a further example, a flavor delivery article can be attached to a cartridge, such as by sliding over an end of the cartridge.

A flavor delivery article can be adapted or configured to provide a single flavor or a plurality of different flavors. In some embodiments, a the flavor delivery article or a device with which the flavor delivery article may combined may be adapted to or configured to provide for control of airflow through the flavor substrate and thus provide user with the ability to select a desired flavor. For example, U.S. patent application Ser. No. 15/935,105, filed Mar. 26, 2018, the disclosure of which is incorporated herein by reference, describes the use of an air flow controller to direct the flow of air, which may be associated with a draw by the user on a mouth piece, selectively through or around one or more a flavor sections.

In one or more embodiments of the present disclosure, an a flavor delivery article can be provided as a "stand-alone" element that may be provided for use with a variety of devices wherein it is desirable to entrain particles or droplets of a flavor liquid into a passing gaseous stream. For example, nebulizers, aerosolizers, medicament delivery devices, heat-not-burn (HNB) smoking articles, carbon tobacco heated products (CTHP), electrical tobacco heated products (ETHP), and the like all may benefit from incorporation of a flavor delivery article as described herein. Accordingly, it is understood that description of the flavor delivery article in combination with an aerosol delivery device is only to provide an example for complete disclosure of the invention, and the use of the flavor delivery article should be viewed as being limited to combination with aerosol delivery devices.

In another aspect, the disclosure can be directed to kits that provide a variety of components as described herein. For example, a kit can comprise a control body with one or more cartridges. A kit further can comprise a control body with one or more charging components. A kit further can comprise a control body with one or more batteries. A kit further can comprise a control body with one or more cartridges and one or more charging components and/or one or more batteries. In further embodiments, a kit can comprise a plurality of cartridges. A kit further can comprise a plurality of cartridges and one or more batteries and/or one or more charging components. The kits further can include a case (or other packaging, carrying, or storage component) that accommodates one or more of the further kit components. The case could be a reusable hard or soft container. Further, the case could be simply a box or other packaging structure. In still further embodiments, the disclosed kits can comprise a mouthpiece as described herein and one or more flavor delivery article as described herein. Further, the kits can comprise a plurality of mouthpieces packaged together for disposable use with an aerosol delivery device. Still further, kits can include one or more mouthpieces and one or more flavor delivery articles and/or one or more cartridges as described herein.

The foregoing description of use of the device can be applied to the various implementations described herein through minor modifications, which can be apparent to the person of skill in the art in light of the further disclosure provided herein. The above description of use, however, is not intended to limit the use of the article but is provided to comply with all necessary requirements of disclosure of the present disclosure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A flavor delivery article comprising:
an outer shell extending along a longitudinal axis between a distal end including at least one opening and a proximal end including at least one opening, the outer shell defining a chamber therein;
a flavor unit positioned in the chamber, the flavor unit extending along a longitudinal axis between a first end and an opposing second end so as to be substantially parallel with the longitudinal axis of the outer shell, the flavor unit comprising at least one flavor substrate configured as a porous sheet, at least one flavor material retained by the flavor substrate, and a film configured substantially as a tube, the porous sheet being one or more of pleated, gathered, and rolled and being positioned within the tube; and
a mouthpiece arranged on the outer shell so as to at least partially cover the proximal end of the outer shell and extend down the outer shell toward the distal end of the outer shell along a portion of a longitudinal length of the outer shell.

2. The flavor delivery article of claim 1, wherein the film is formed of a polymeric material.

3. The flavor delivery article of claim 2, wherein the polymeric material is selected from the group consisting of polyesters, acetals, polycarbonates, celluloses, polyvinylidene fluoride (PVDF), low density polyethylene (LDPE), high density polyethylene (HDPE), polyvinylchloride (PVC), polytetrafluoroethylene (PTFE), polylactic acid (PLA), polyethylene terephthalate (PET), and combinations thereof.

4. The flavor delivery article of claim 1, wherein the film is formed of a material selected from the group consisting of paper foil, filter paper, ceramics, aluminum, and combinations thereof.

5. The flavor delivery article of claim 1, wherein the film has a thickness of about 2 microns to about 500 microns.

6. The flavor delivery article of claim 1, wherein the at least one elongated flavor substrate has a graded porosity such that an average pore size varies across at least a portion of the at least one elongated flavor substrate.

7. The flavor delivery article of claim 1, wherein the porous material forming the at least one elongated flavor substrate is a polymeric material.

8. The flavor delivery article of claim 7, wherein the polymeric material is selected from the group consisting of polyethersulfone, polypropylene, polyethylene, polyester, nylon, polylactic acid (PLA), cellulose nitrate, regenerated cellulose, cellulose acetate, silica, cotton, and combinations thereof.

9. The flavor delivery article of claim 1, wherein one or both of the following conditions is met:
the at least one elongated flavor substrate comprises one or more rods comprising a porous material;
the at least one elongated flavor substrate comprises one or more tubes comprising a porous material.

10. The flavor delivery article of claim 1, wherein at least a portion of the outer shell is shaped and dimensioned for insertion into a cartridge of an aerosol delivery device.

11. A cartridge for an aerosol delivery device, the cartridge comprising:
a cartridge housing having a mouthend;
a reservoir including an aerosol precursor composition;
a heater adapted to vaporize the aerosol precursor composition; and
a flavor delivery article according to claim 1 engaged with the cartridge such that at least the distal end of the outer shell is engaged with the mouthend of the cartridge housing.

12. The cartridge of claim 11, further comprising a liquid transport element configured for transport of the aerosol precursor composition between a reservoir and the heater.

13. The cartridge of claim 11, wherein the reservoir includes a fibrous material.

14. The cartridge of claim 11, wherein the reservoir is a tank.

15. An aerosol delivery device comprising:
a power unit housing including a power source and a controller; and
a cartridge according to claim 11.

16. The flavor delivery article of claim 1, wherein the mouthpiece comprises a mouth opening configured to the passage of vapor or aerosol therethrough.

17. The flavor delivery article of claim 16, wherein the mouth opening is configured to retain the flavor substrate and comprises a plurality of apertures, a mesh, a screen, or a combination thereof.

18. The flavor delivery article of claim 1, wherein the mouthpiece is configured to be removably attached to the outer shell.

19. The flavor delivery article of claim 6, wherein the average pore size changes from a first portion of the flavor substrate to a second portion of the flavor substrate.

20. The flavor delivery article of claim 19, wherein the first portion and the second portion are selected from an inner section of the flavor substrate and an outer section of the flavor substrate.

21. The flavor delivery article of claim 6, wherein the average size of the pores is about 250 nm to about 2 $\mu$m.

22. The flavor delivery article of claim 6, wherein the average size of the pores is about 1 $\mu$m to about 20 $\mu$m.

23. The flavor deliver of claim 6, wherein the average size of the pores is about 1 nm to about 30 $\mu$m.

* * * * *